(12) United States Patent
Castillo (10) Patent No.: US 10,598,011 B2
(45) Date of Patent: Mar. 24, 2020

(54) SEGMENTED WIRELESS PRODUCTION LOGGING

(71) Applicant: BAKER HUGHES INCORPORATED, Houston, TX (US)

(72) Inventor: Homero Castillo, Kingwood, TX (US)

(73) Assignee: Baker Hughes Incorporated, Houston, TX (US)

( * ) Notice: Subject to any disclaimer, the term of this patent is extended or adjusted under 35 U.S.C. 154(b) by 156 days.

(21) Appl. No.: 15/236,566

(22) Filed: Aug. 15, 2016

(65) Prior Publication Data

US 2018/0045045 A1 Feb. 15, 2018

(51) Int. Cl.
| | |
|---|---|
| E21B 49/08 | (2006.01) |
| E21B 47/01 | (2012.01) |
| E21B 23/00 | (2006.01) |
| E21B 47/00 | (2012.01) |
| E21B 47/06 | (2012.01) |
| E21B 49/00 | (2006.01) |
| G01N 15/08 | (2006.01) |

(52) U.S. Cl.
CPC .............. *E21B 49/08* (2013.01); *E21B 23/00* (2013.01); *E21B 47/00* (2013.01); *E21B 47/01* (2013.01); *E21B 47/06* (2013.01); *E21B 47/065* (2013.01); *E21B 49/00* (2013.01); *G01N 15/088* (2013.01)

(58) Field of Classification Search
CPC ........ E21B 47/00; E21B 47/06; E21B 47/065; E21B 47/12; E21B 49/00; E21B 49/003
USPC .............. 73/152.05, 152.18, 152.19, 152.21, 73/152.22, 152.29
See application file for complete search history.

(56) References Cited

U.S. PATENT DOCUMENTS

| | | | | |
|---|---|---|---|---|
| 4,435,978 | A * | 3/1984 | Glatz | E21B 47/1005 166/250.01 |
| 7,894,297 | B2 | 2/2011 | Nutt et al. | |
| 9,069,099 | B2 | 6/2015 | Auzerais et al. | |
| 2007/0187092 | A1* | 8/2007 | Mullins | E21B 47/06 166/252.1 |
| 2007/0215345 | A1* | 9/2007 | Lafferty | E21B 43/26 166/250.1 |
| 2008/0156485 | A1* | 7/2008 | Phillips | E21B 23/08 166/254.2 |

(Continued)

FOREIGN PATENT DOCUMENTS

WO 2007105167 A2 9/2007

OTHER PUBLICATIONS

International Search Report and Written Opinion dated Nov. 6, 2017 for corresponding PCT/US2017/046368.

(Continued)

*Primary Examiner* — Benjamin R Schmitt
(74) *Attorney, Agent, or Firm* — Hogan Lovells US LLP (57) ABSTRACT

A system and method for logging in a wellbore where sensor assemblies on a logging tool are deployed and landed in the wellbore. After the sensor assemblies are landed in the wellbore and released from the logging tool, the logging tool is pulled uphole. Moving the logging tool uphole from where the sensor assemblies are landed, reduces interference of the logging tool with measurements obtained with the sensor assemblies. The sensor assemblies include sensors for detecting fluid flow, pressure, temperature, fluid density, formation resistivity, and which can be mechanical, optical, acoustic, or electromagnetic.

7 Claims, 8 Drawing Sheets

(56) References Cited

U.S. PATENT DOCUMENTS

| | | | |
|---|---|---|---|
| 2011/0188348 A1* | 8/2011 | Auzerais | G01V 1/40 |
| | | | 367/86 |
| 2015/0377009 A1 | 12/2015 | Frosell | |
| 2016/0130935 A1 | 5/2016 | Manzar et al. | |

OTHER PUBLICATIONS

International Preliminary Report on Patentability dated Feb. 28, 2019 in corresponding PCT Application No. PCT/US2017/046368.

* cited by examiner

SEGMENTED WIRELESS PRODUCTION LOGGING

BACKGROUND OF THE INVENTION

1. Field of Invention

The present disclosure relates to production logging. More specifically, the present disclosure relates to a system and method of deploying sensors in a hydrocarbon producing wellbore, sensing wellbore conditions with the sensors, and retrieving the sensors.

2. Description of Prior Art

Various types of devices are disposed downhole for monitoring parameters of fluid flowing within a wellbore, and evaluating subterranean formation adjacent the wellbore. Typically fluid parameters monitored downhole include a flowrate of fluid flowing downhole, fluid properties, and fluid conditions. Fluid properties monitored generally include fluid density, composition, and viscosity, and fluid conditions monitored usually include fluid pressure and fluid temperature. The formation properties typically estimated are resistivity, rugosity, and porosity. Flowmeters are typically used for measuring fluid flow, and sensors are typically used for measuring fluid properties and/or conditions. The flowmeters and sensors are deployed downhole within a producing wellbore, a jumper/caisson used in conjunction with a subsea wellbore, or a production transmission line used in distributing the produced fluids. Formation properties are typically measured with nuclear or electromagnetic tools. Monitoring fluid produced from a wellbore, and the formation properties, is useful in wellbore evaluation and to project production life of a well. Fluid density and viscosity are usually measured to estimate the type of fluid flowing in the monitored portion of the wellbore, i.e. oil, water, gas. A further determination of the fluid downhole can be verified by readings of temperature and/or pressure.

As is known, the downhole in-situ conditions of temperature and pressure can change significantly depending on the location in the borehole. Fluid properties, such as viscosity and density are dependent on fluid temperature and pressure, thus these properties for the same fluid can change depending on where the fluid is in the wellbore. Additionally, dissimilar types of fluids that are connate in the formation can migrate into the wellbore, thereby further altering the properties of the fluid flowing in the wellbore. Currently, downhole sensors for measuring fluid properties and sensors for measuring flow are disposed at different places in the wellbore or are spaced sufficiently far apart from one another that the fluid being monitored has different fluid properties when evaluated by these spaced apart sensors. Accordingly, these readings are susceptible to error if a flow rate calculation is based on an inaccurate value of fluid property. Permanently disposed sensors partially obstruct fluid flow in the wellbore, which can increase pressure drop of fluid being produced. Further, temporary sensors are mounted onto downhole tools, where the presence of the downhole tool affects the measurements obtained by the sensors.

SUMMARY OF THE INVENTION

Disclosed herein is an example of a logging tool for use in a wellbore and which includes a mother tool, a stinger depending from an end of the mother tool, and a sensor assembly selectively coupled to and decoupled from the stinger with a latch, and that is selectively landed in a designated location in the wellbore when decoupled from the stinger. The sensor assembly can be a sensor element for sensing a fluid; or can be one or more of a flow meter, a temperature sensor, a pressure sensor, or a density sensor. Optionally, the sensor assembly is a sensor for sensing a formation; which can be one or more of a resistivity sensor, a porosity sensor, and a rugosity sensor. The logging tool can further include proximity sensors on the sensor assembly and the stinger, so that when the mother tool is separated from the landed sensor assembly and being moved towards the sensor assembly in the wellbore, signals from the proximity sensors indicate relative locations of the sensor assembly and the stinger. In one alternative, the sensor assembly is in a retracted configuration and set radially inward from walls of the wellbore when the logging tool is being lowered in the wellbore, and wherein the sensor assembly is in a deployed configuration and in engaging contact with the walls of the wellbore when landed in the wellbore. The logging tool can further optionally include a plurality of additional sensor assemblies, so that the sensor assembly and the plurality of additional sensor assemblies make up a sensor set. In one specific example, the sensor assembly is formed from a hub that circumscribes the stinger when the sensor assembly is coupled with the stinger, arms that have an end connected to the hub and that project axially away from the hub when the sensor assembly is in a retracted configuration, the arms projecting radially away from the hub when the sensor assembly is in a deployed configuration, and sensor elements on the arms. A tool controller can be included and that is for controlling the latch, so that when the tool controller transmits a signal to the latch, the sensor assembly is decoupled from the stinger, and when the tool controller transmits another signal to the latch, the sensor assembly is coupled to the stinger.

Another example of a logging tool for use in a wellbore is described herein and that includes a mother tool having an upper end connected to a conveyance element, a sensor assembly selectively coupled to and decoupled from the mother tool, and a communication system in communication between the sensor assembly and mother tool. This example of the logging tool can further include an elongated stinger extending from an end of the mother tool distal from the upper end. The communication system can include a transceiver that is coupled with the mother tool and a transceiver that is coupled with the sensor assembly. In this example, the sensor assembly is made up of sensor elements that are in communication with the transceiver that is coupled with the sensor assembly.

Also described herein is a method of logging in a wellbore and which involves deploying a mother tool with a sensor in the wellbore, decoupling the sensor from the mother tool and anchoring the sensor at a designated depth in the wellbore, moving the mother tool uphole from where the sensor is anchored in the wellbore, and communicating between the mother tool and sensor. The method can further include moving the mother tool downhole and recoupling the sensor to the mother tool. Optionally included with the method is a step of sensing a proximity between the mother tool and the sensor when the sensor decoupled from the mother tool. The sensor can be a plurality of sensors that are spaced apart from one another on the mother tool when the mother tool is deployed in the wellbore, and that are decoupled from the mother tool and anchored in the wellbore at different depths of the wellbore. Optionally, the sensor senses data in the wellbore and communicates the data to the mother tool;

where the data in the wellbore can be fluid pressure, fluid temperature, fluid flow, formation porosity, and formation resistivity.

BRIEF DESCRIPTION OF DRAWINGS

Some of the features and benefits of the present invention having been stated, others will become apparent as the description proceeds when taken in conjunction with the accompanying drawings, in which.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF INVENTION

The method and system of the present disclosure will now be described more fully hereinafter with reference to the accompanying drawings in which embodiments are shown. The method and system of the present disclosure may be in many different forms and should not be construed as limited to the illustrated embodiments set forth herein; rather, these embodiments are provided so that this disclosure will be thorough and complete, and will fully convey its scope to those skilled in the art. Like numbers refer to like elements throughout. In an embodiment, usage of the term "about" includes +/−5% of the cited magnitude. In an embodiment, usage of the term "substantially" includes +/−5% of the cited magnitude.

It is to be further understood that the scope of the present disclosure is not limited to the exact details of construction, operation, exact materials, or embodiments shown and described, as modifications and equivalents will be apparent to one skilled in the art. In the drawings and specification, there have been disclosed illustrative embodiments and, although specific terms are employed, they are used in a generic and descriptive sense only and not for the purpose of limitation.

Figures 1, 2A:
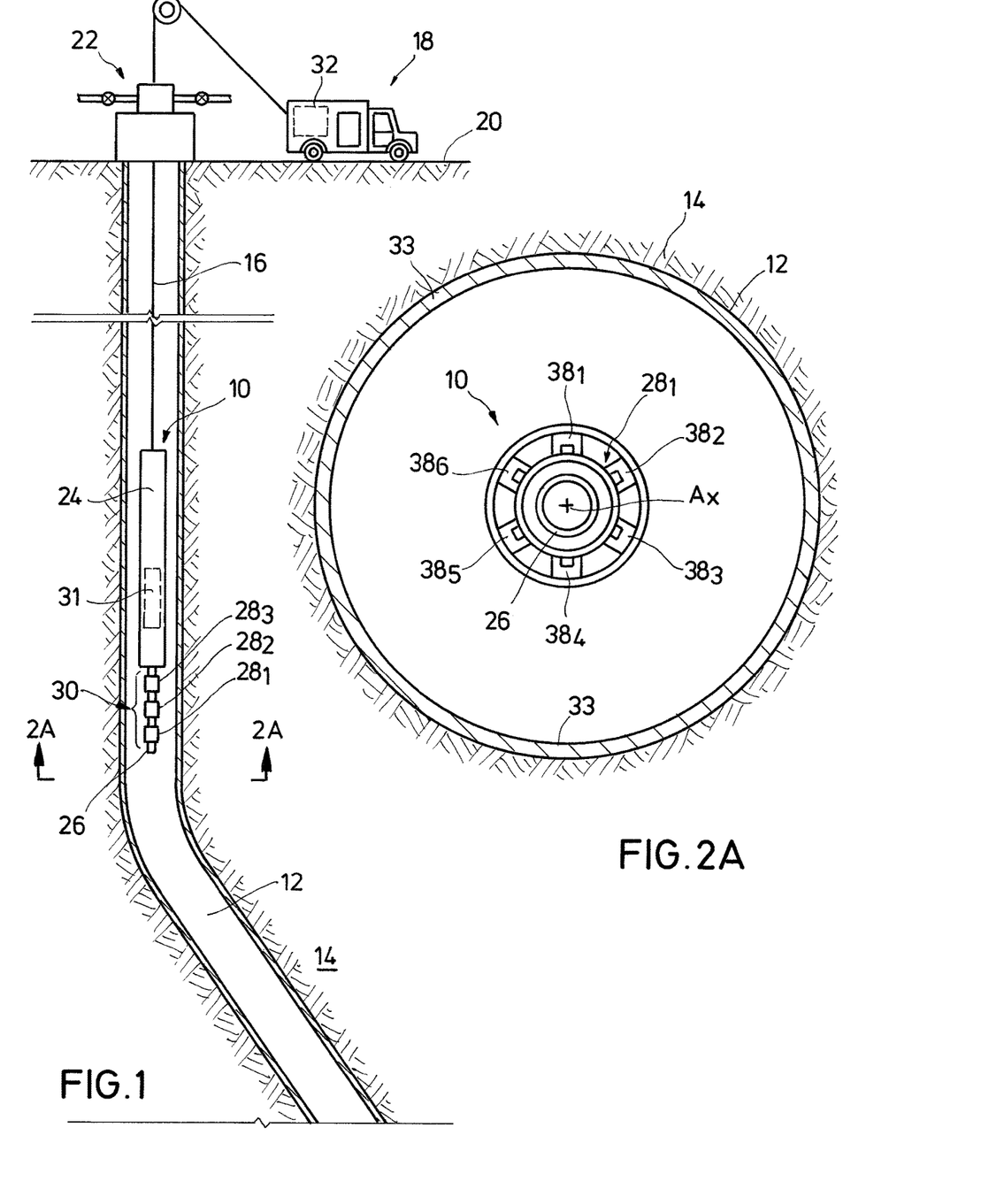
FIG. 1 is a side partial sectional view of an example of a logging tool having a sensor set of sensor assemblies, and disposed in a wellbore.
FIG. 2A, which is taken along lines 2A-2A of FIG. 1, is an axial view of an example of a sensor assembly of FIG. 1 in a retracted configuration.

Depicted in side sectional view in FIG. 1 is an example of a downhole tool 10 within a wellbore 12, wherein the wellbore 12 intersects a formation 14. The downhole tool 10 is shown suspended from a wireline 16, which is used to deploy the downhole tool 10, and through which communication to and from the downhole tool 10 is transmitted. Alternate conveyance means may be used for inserting and retrieving the downhole tool 10 from wellbore 12, such as coiled tubing, slick line, cable and the like. An end of wireline 16 opposite from its connection to downhole tool 10 is shown within a service truck 18 provided on the surface 20 and adjacent an opening of wellbore 12. Wireline 16 is threaded through a wellhead assembly 22 which is mounted on surface 20 and over the wellbore 12. In the example of FIG. 1, the downhole tool 10 includes a mother tool 24 which has a generally cylindrical outer profile, and an elongated stinger 26 shown depending from an end of the mother tool 24 opposite to where it connects to wireline 16. Sensor assemblies $28_{1-3}$ are shown mounted on and coupled to stinger 26 and which define a sensor set 30. As will be described in more detail below, coupling and decoupling of sensor assemblies $28_{1-3}$ from stinger 26 can be controlled by a tool controller 31 which is depicted in dashed outline and disposed within mother tool 24. Tool controller 31 is in selective communication with a surface controller 32 shown disposed within service truck 18. Communication between the controllers 31, 32 can be along communication means (i.e. conductive media or fiber optics) in wireline 16, or wireless along the wellbore 12.

FIG. 2A, which is taken along lines 2A-2A on FIG. 1, shows in an axial sectional view an upward looking example of the lower end of downhole tool 10 disposed within wellbore 12. In the illustrated example, casing 33 is shown lining the walls of wellbore 12. Here, the sensor assembly $28_1$ is in a retracted configuration, so that its outer periphery is spaced radially inward from an inner surface of the casing 33. In one example, while in the retracted configuration, the sensor assembly $28_1$ is coupled to the stinger 26.

Figures 2B, 3:
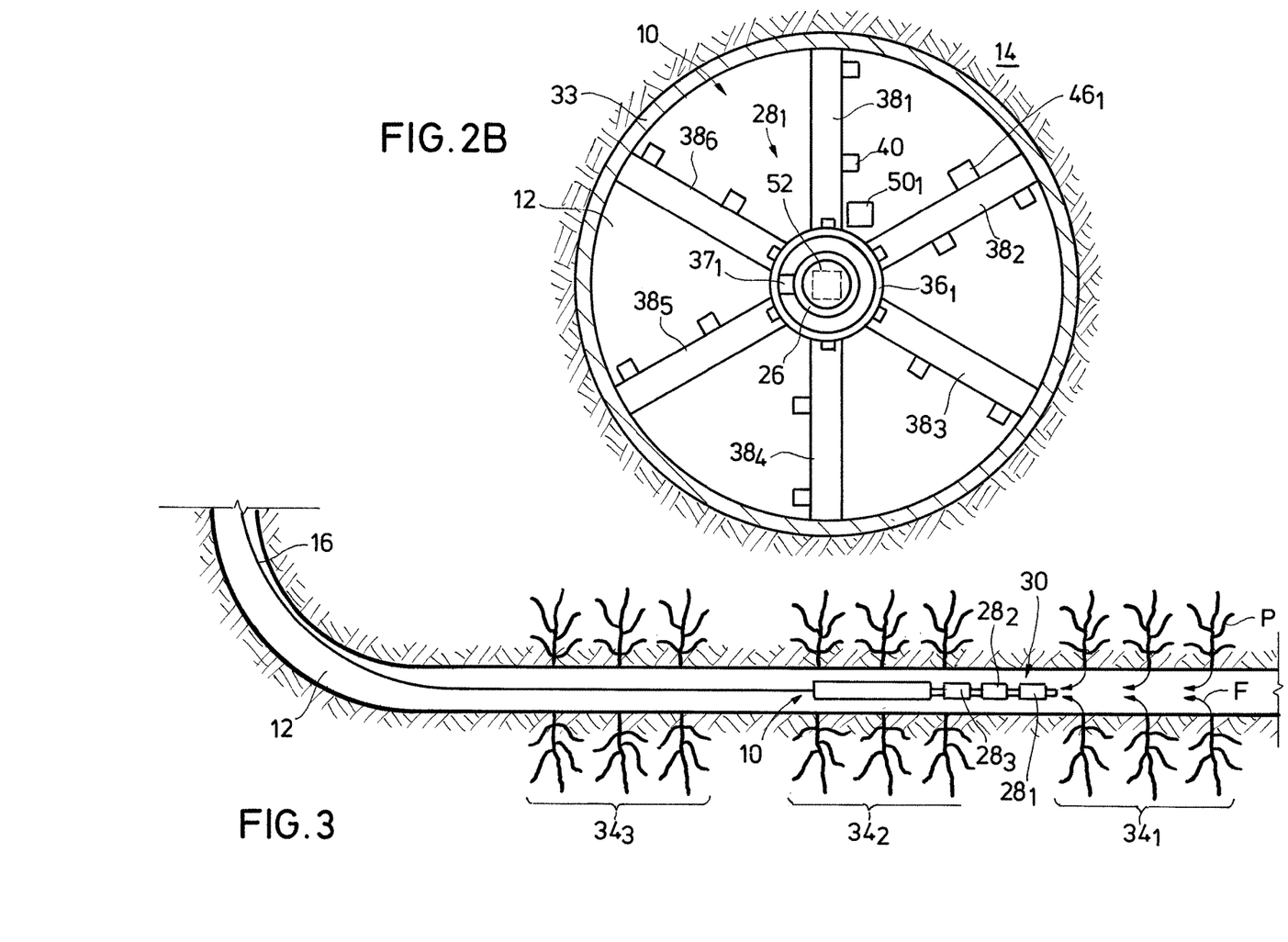
FIG. 2B, which is taken along lines 2B-2B of FIG. 4, is an axial view of an example of a sensor assembly in a deployed configuration.
FIGS. 3-8 are side sectional views of an example of the logging tool deploying and landing the sensor assemblies of FIG. 1 in a deviated portion of the wellbore.

FIG. 3 shows in a side sectional view the downhole tool 10 with sensor assemblies $28_{1-3}$ in a deviated section of wellbore 12 and being guided past a series of perforation arrays $34_{1-3}$. The perforation arrays $34_{1-3}$ are made up of a number of perforations P, which are openings in the formation 14 that extend radially outward from the wellbore 12. Connate fluid F in the formation 14 flows into the wellbore 12 through the perforations P.

Figure 4:
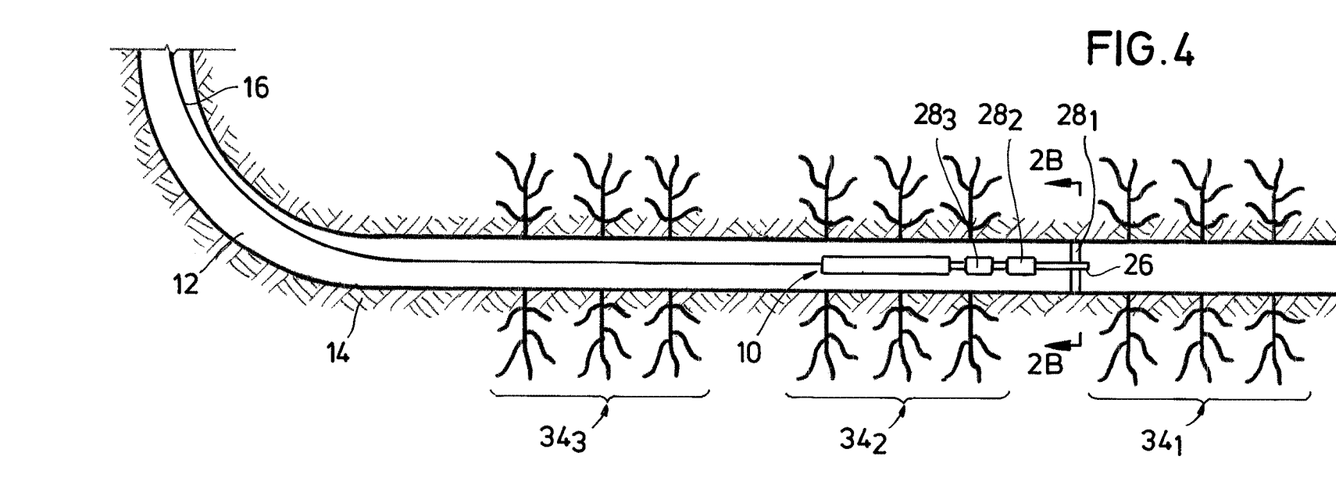

FIG. 4 illustrates in side sectional view, an example of sensor assembly $28_1$ having been radially expanded into a deployed configuration and anchored within wellbore 12 between perforation arrays $34_1$ and perforation array $34_2$. In an alternative, the sensor assembly $28_1$ is deployed when the downhole tool 10 is at a designated depth in the wellbore 12. FIG. 2B, which is taken along lines 2B-2B of FIG. 4, shows an axial sectional view of an example of sensor assembly $28_1$ in the deployed configuration. In the deployed configuration, the outer periphery of sensor assembly $28_1$ is in contact with and anchored to the walls of wellbore 12, and as shown are in close contact with the inner surface of casing 33. Further, when in the deployed configuration, sensor assembly $28_1$ is decoupled from stinger 26 so that downhole tool 10 can be moved within wellbore 12 while sensor assembly $28_1$ remains anchored in a designated depth of wellbore 12. Optionally, production tubing (not shown) is inserted within the casing 33 and provides a flow conduit for conveying the connate fluid F to surface. In this example, the downhole tool 10 is inserted into the production tubing.

Figure 5:
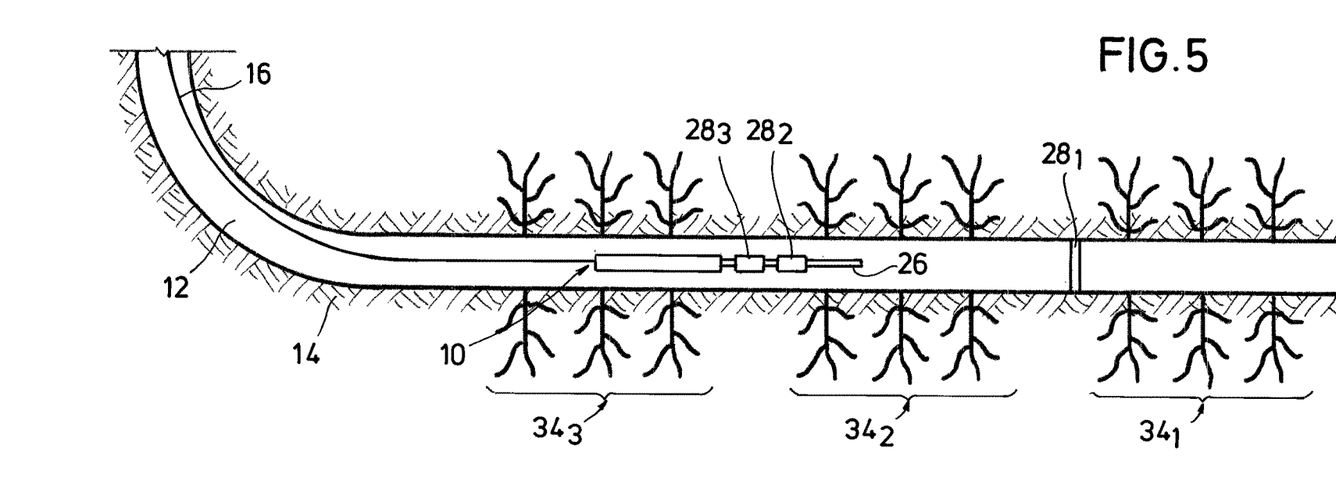
Figure 6:
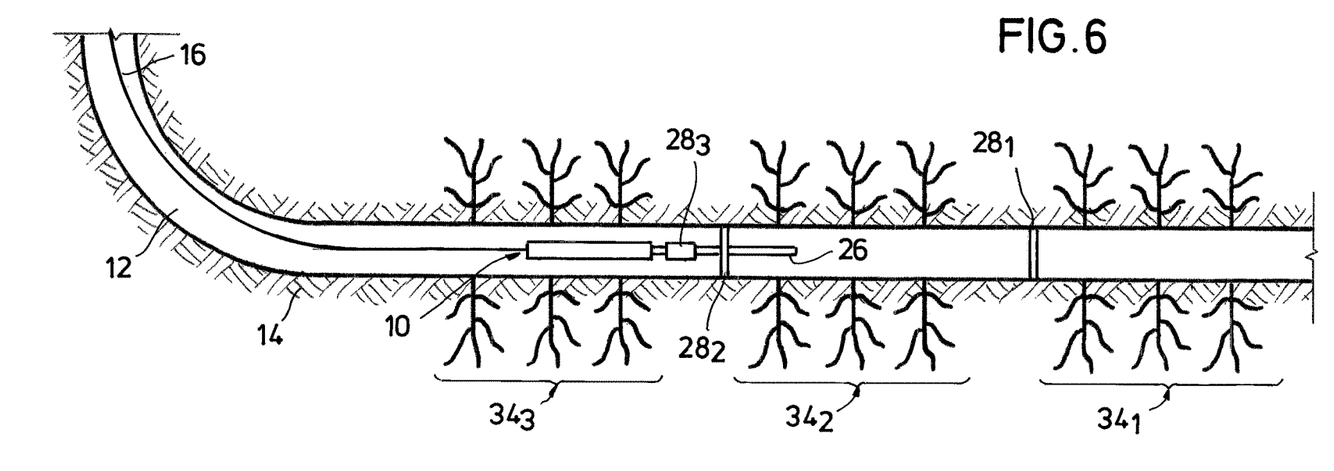
Figure 7:
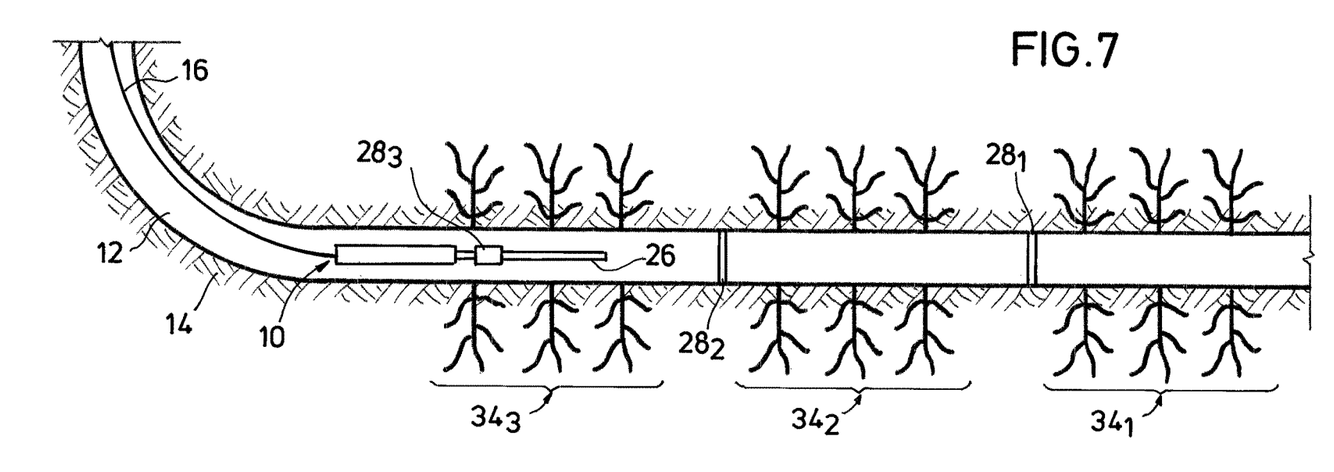
Figure 8:
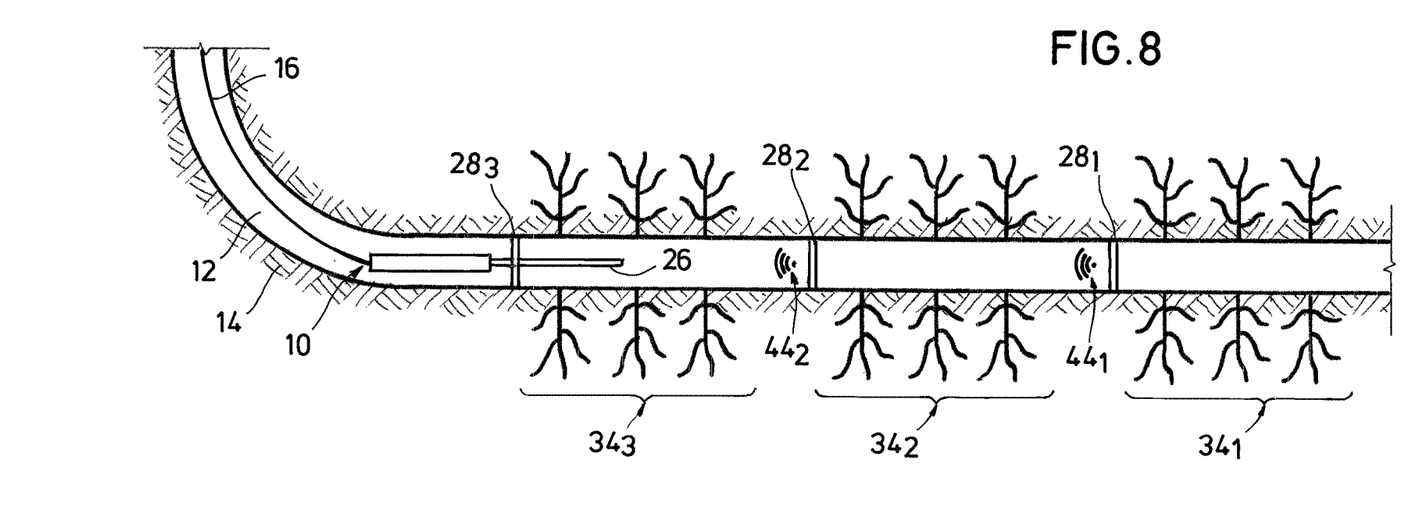

Shown in FIG. 5 is an example of operation where the downhole tool 10 is drawn up hole within wellbore 12 after the sensor assembly $28_1$ is put into the deployed configuration and anchored in the wellbore 12. Referring to FIG. 6, sensor assembly $28_2$ is shown converted into the deployed configuration and anchored within wellbore 12. In the example of FIG. 6, sensor assembly $28_2$ is anchored in a portion of the wellbore 12 that is between perforation arrays $34_2$, $34_3$. In the example of FIG. 7 downhole tool 10 is drawn further up hole within wellbore 12 after sensor assembly $28_2$ is deployed and anchored in wellbore 12, and decoupled from stinger 26. FIG. 8 illustrates an embodiment where sensor assembly $28_3$ is set in the deployed configuration and in anchoring contact with sidewalls of wellbore 12. In the example of FIG. 8, sensor assembly $28_3$ is disposed in wellbore 12 on a side of perforation array $34_3$ opposite from perforation array $34_2$.

Figure 9:
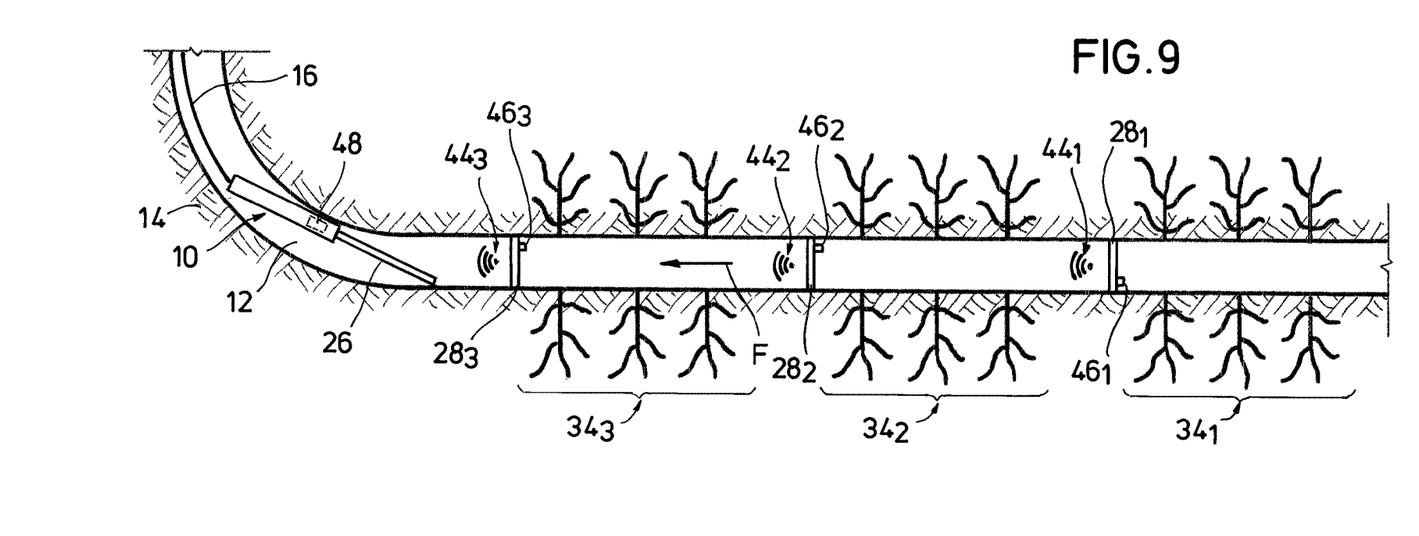
FIG. 9 is a side sectional view of an example of the sensor assemblies being landed and sensing conditions in the wellbore.

FIG. 9 depicts an alternative where sensor assembly $28_3$ is decoupled from stinger 26, and the downhole tool 10 drawn further up hole in wellbore 12 and away from sensor assembly $28_3$. In the illustrated embodiment, sensor assemblies $28_{1-3}$ are spaced apart from one another at different depths within wellbore 12 and at designated locations. As shown, the sensor assemblies $28_{1-3}$ are strategically disposed between the perforation arrays $34_{1-3}$ and can selectively monitor wellbore conditions, formation properties, fluid properties, and fluid flow in sections of the wellbore 12 that are between the perforation arrays $34_{1-3}$. In an alternative, the selective monitoring in these discrete locations provides estimated flow measurement and fluid properties from each of these perforation arrays $34_{1-3}$ individually. Moreover, the anchoring of the sensor arrays $28_{1-3}$ without the presence of the downhole tool 10, results in more accurate measurements of flow of fluid F through wellbore 12 without interference from the downhole tool 10.

Referring back to FIG. 2B, each of the sensor assemblies, as illustrated by sensor assembly $28_1$ in the deployed configuration, are shown to have a hub 36 which is selectively coupled to the stinger 26 by a latch mechanism $37_1$. Multiple examples of a latch $37_1$ can be understood by those skilled in the art, such as dogs, tabs, collets, and the like. Thus when activated, latch $37_1$ engages hub 36, which couples sensor assembly $28_1$ to stinger 26. Control commands can cause latch $37_1$ to retract thereby allowing stinger 26 to move axially with respect to hub 36 and sensor assembly $28_1$ thereby allowing downhole tool 10 to move within the wellbore 12 with respect to the sensor assembly $28_1$. Further included with the sensor assemblies $28_{1-3}$ are arms $38_{1-6}$ which are elongate members whose elongate lengths project radially outward from hub 36 and into contact with the inner walls of wellbore 12 when sensor assembly $28_1$ is in the deployed configuration. Referring back to FIG. 2A, arms $38_{1-6}$ project generally oblique to an axis $A_X$ of downhole tool 10 when in the retracted configuration, thereby allowing deployment of downhole tool 10 within wellbore 12. Referring back to FIG. 2B, sensor elements 40 are shown coupled on the arms $38_{1-6}$ at various radial locations on the arms $38_{1-6}$. The sensor elements 40 can be one or more of temperature sensors, pressure sensors, flow elements which can sense fluid flow temperature, fluid flow pressure, fluid flow rate, or any other measurable parameter of the fluid F in the wellbore 12. Other examples of sensor elements 40 include sensors for sensing properties of the formation 14 adjacent wellbore 12; where examples of formation properties include porosity, density, resistivity, and rugosity. However, the sensor elements 40 can be used for sensing any downhole condition and whose use is not limited to that provided herein. Other examples of what can be measured by the sensor elements includes fluid type, fluid speed, fluid density, fluid viscosity, fluid acoustic properties, fluid electrical properties, fluid radioactive properties, fluid magnetic resonance properties, fluid optical properties, an amount of fluid flow, formation porosity, and formation resistivity In a non-limiting example of operation as shown in FIG. 9, signals $44_{1-3}$ are shown being transmitted within wellbore 12 between the sensor assemblies $28_{1-3}$ and downhole tool 10. Transmission and/or receipt of the signals $44_{1-3}$ is selectively performed by transceivers $46_{1-3}$ shown disposed respectively on the sensor assemblies $28_{1-3}$, and transceiver 48 that is provided within the mother tool 10. Thus, data as described above can be sensed or collected by sensor assemblies $28_{1-3}$ and transmitted to transceiver 48 from transceivers $46_{1-3}$ and then communicated up hole via wireline 16 for storage and/or processing. Alternatively, less than all of the sensor assemblies $28_{1-3}$ can be operating at one time and so that less than the number of signals illustrated in FIG. 9 can be transmitted between sensor assemblies $28_{1-3}$ and downhole tool 10. Optionally, signals or data can be transmitted from transceiver 48 to sensor assemblies $28_{1-3}$ for adjusting operation of the particular sensor assemblies $28_{1-3}$. In another example, data sensed by sensor assemblies $28_{1-3}$ can be stored in data storage media (not shown) provided with the sensor assemblies $28_{1-3}$. Yet further optionally, the number of sensor assemblies $28_{1-3}$ provided for use with the downhole tool 10 can be three as shown, greater than three, or less than three. In another alternate example, the signals $44_{1-3}$ can be transmitted fully up hole and so that communication is directly between the sensor assemblies $28_{1-3}$ and surface controller 32 of FIG. 1. Further, the positioning of the sensor assemblies $28_{1-3}$ is not limited to the locations, spacing, or arrangements as shown. Instead, sensor assemblies $28_{1-3}$ can be disposed adjacent one of the perforation arrays $34_{1-3}$ rather than between, and more than one of the sensor assemblies $28_{1-3}$ can be disposed proximate one another rather than spaced apart as shown.

Figure 10:
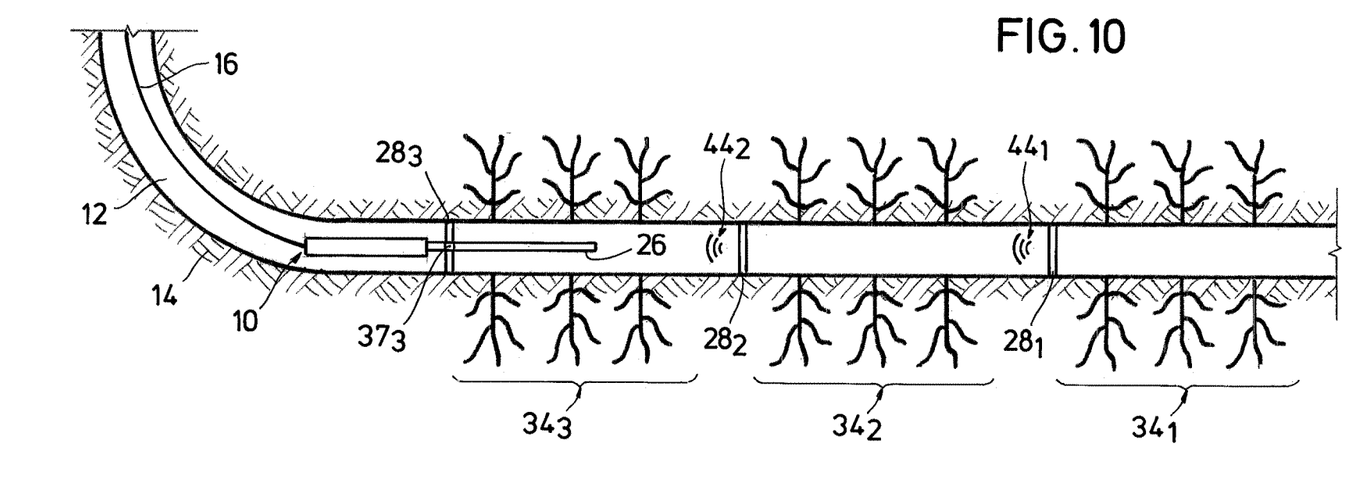
FIGS. 10-15 are side sectional views of the logging tool of FIG. 1 retrieving the sensor set of sensor assemblies.
Figure 11:
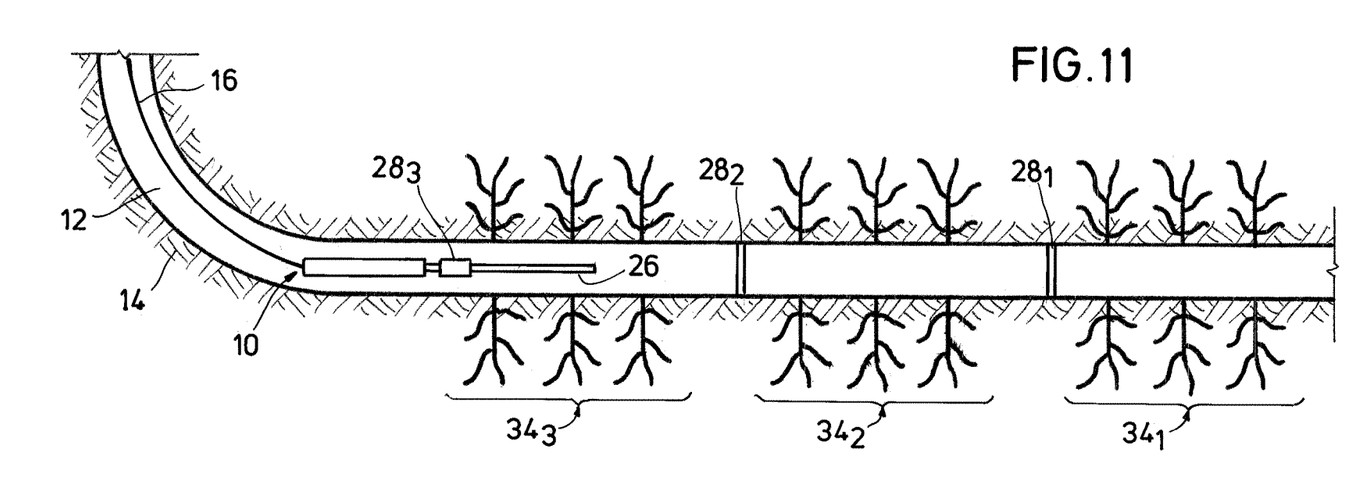
Figure 12:
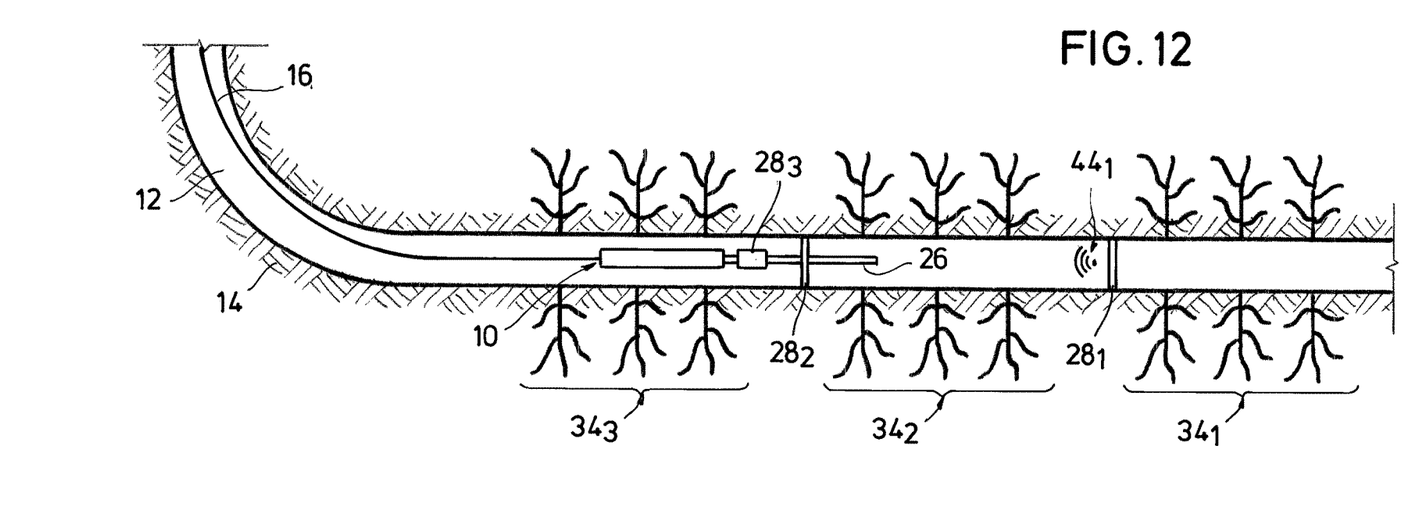
Figure 13:
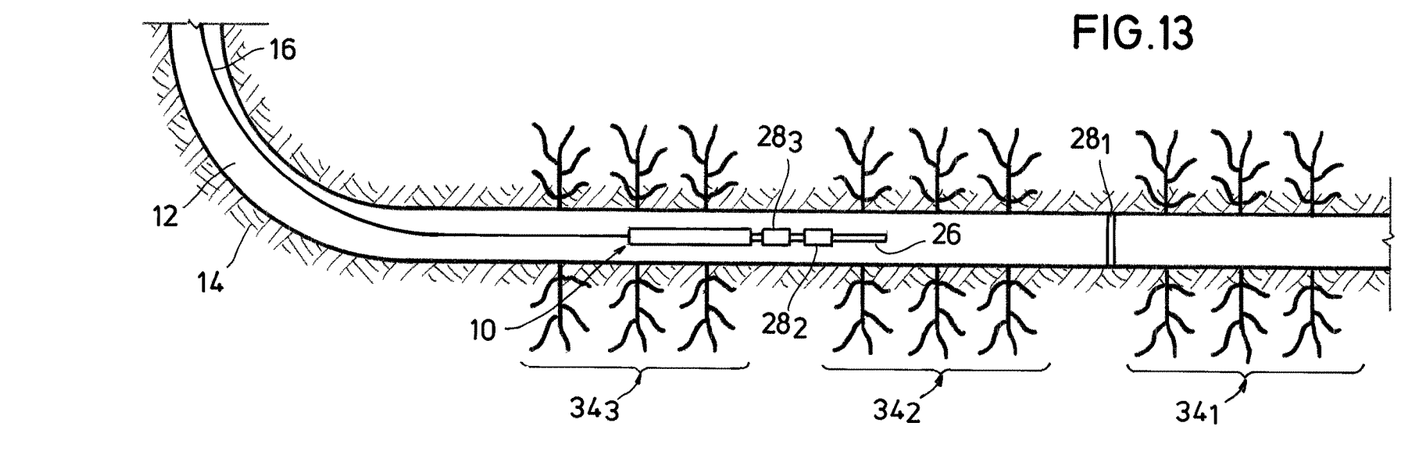
Figure 14:
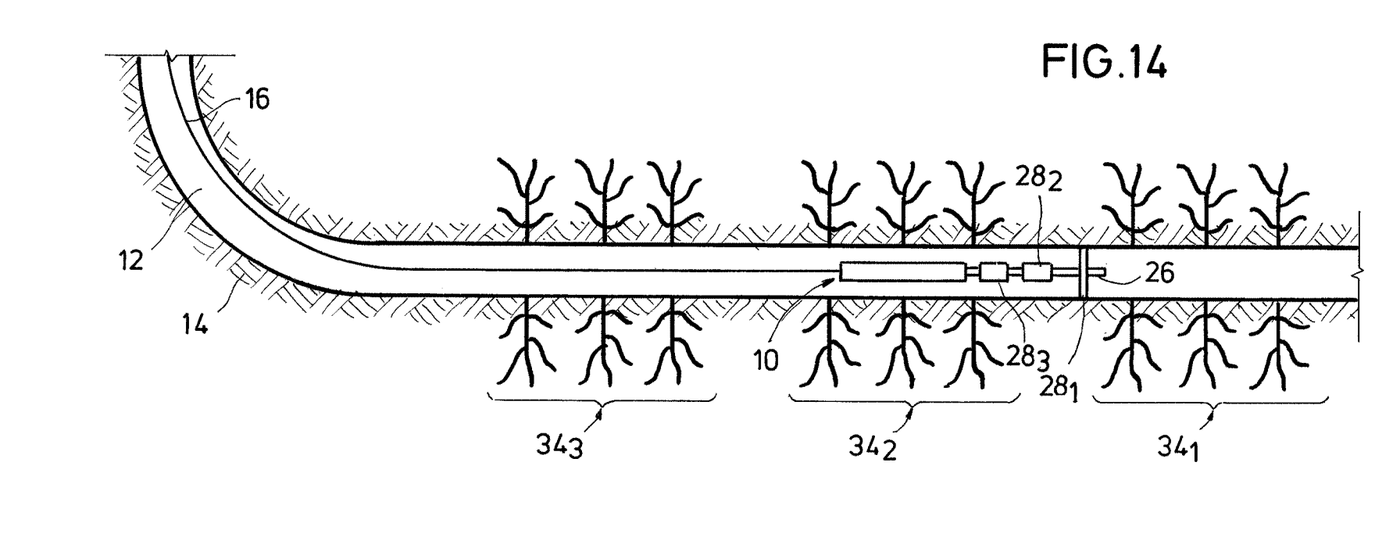
Figure 15:
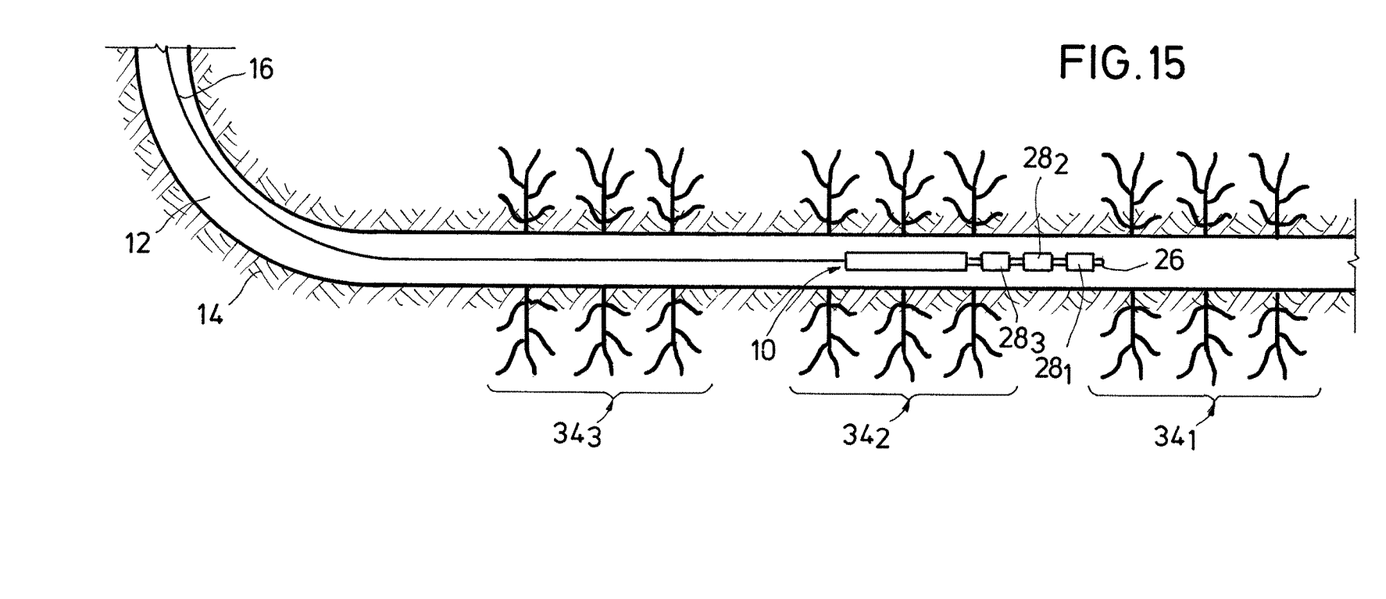

FIG. 10 shows in a side sectional view an example of the downhole tool 10 being moved back downhole from its position of FIG. 9, and the stinger 26 being reinserted into sensor assembly $28_3$. Sensor assembly $28_3$ recouples to downhole tool 10 after being engaged by stinger 26, in an example latch $37_3$ is selectively activated to affix sensor assembly $28_3$ to stinger 26. Further, sensors $28_1$, $28_2$ can still be sending signals $44_1$, $44_2$ during this process and continuing to sense data and conditions within borehole 12. FIG. 11 depicts an example where sensor assembly $28_3$ is in the retracted configuration on stinger 26 so that as shown in FIG. 12, further downhole movement of downhole tool brings the stinger 26 into contact with sensor assembly $28_2$. Signal $44_1$ is shown in wellbore illustrating that sensor assembly $28_1$ and downhole tool 10 can be in communication with one another. In an example, signals $44_{1-3}$ are wireless, which can be electromagnetic waves as well as mud pulses and the like. Optionally, hard wire examples exist wherein the sensor assemblies $28_{1-3}$ maintain communication via conductive elements throughout the process of deployment and retrieval of the sensor assemblies $28_{1-3}$. In one example, one or more of the sensor assemblies $28_{1-3}$ operates as a transponder that performs a wireless repeater function to allow communication between one or more of the other sensor assemblies $28_{1-3}$ and the downhole tool 10 should the distance between the downhole tool 10 and the other sensors assemblies $28_{1-3}$ exceeds its operating range. FIG. 13 depicts an example where sensor assembly $28_2$ is configured into its retracted configuration and so that downhole tool 10 can move deeper into the wellbore 12 and retrieve downhole assemblies $28_{1-3}$ as illustrated in FIGS. 14 and 15.

Referring back to FIG. 2B, optional proximity sensors $50_1$ and 52 are illustrated, which can facilitate the coupling of stinger 26 to the sensor assemblies $28_1$. In an example of operation, proximity sensors $50_1$, 52 sense their relative proximity to one another and generate signals reflective of the relative proximity of stinger 26 to sensor array $28_1$, which can be used by operations personnel to guide stinger 26 into hub 36 of sensor array $28_1$. Similarly, proximity sensors (not shown) can also be provided on other sensor arrays $28_{2,3}$ (FIG. 3) so that downhole tool 10 can be guided to recouple the sensor arrays $28_{2,3}$ to the stinger 26 so they can be retrieved to surface 20. Optionally, transceivers $46_{1-3}$, 48 (FIG. 9) can be in communication with one another in order to provide guiding signals for reattaching sensor arrays $28_{1-3}$ to downhole tool 10.

In an alternate embodiment, each of the sensor assemblies $28_{1-3}$ of the sensor set 30 of FIG. 1 are equipped with latching systems (not shown) for coupling to one another. Thus in this example, the stinger 26 can optionally be omitted from the tool 10 and one of the sensor assemblies $28_{1-3}$ configured to be coupled directly to the mother tool 24, and the remaining sensor assemblies $28_{1-3}$ couple to one another, so that the sensor set 30 depends directly from the mother tool 24. Moreover, the sensor assemblies $28_{1-3}$ can also be electrical and signal communication with one another independently or through the latching system. In one embodiment, a downhole setting tool (not shown), such as those currently used for setting and retrieving an inflatable plug, is included with the tool 10. In this example, a driving tool is set in each of the sensor assemblies $28_{1-3}$, such as within a receptacle, and that rotates to set and release the particular one of the sensor assemblies $28_{1-3}$. The setting tool can also be used to retrieve the sensor assemblies $28_{1-3}$ where the driving tool inserts into the sensor assemblies $28_{1-3}$ and rotated to retract the sensor assemblies $28_{1-3}$ and then retrieve them from the wellbore 12. In one example, each of the sensor assemblies $28_{1-3}$ includes an electrical motor and gear box, that when selectively energized provides power to the sensor assemblies $28_{1-3}$ for orienting them into the set and unset configurations. An inductively coupled electrical power receiver/repeater scheme can also be included in this configuration.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. These and other similar modifications will readily suggest themselves to those skilled in the art, and are intended to be encompassed within the spirit of the present invention disclosed herein and the scope of the appended claims.

What is claimed is:

1. A method of logging in a wellbore comprising:
   deploying a mother tool with attached first and second sensors into the wellbore;
   detaching the first sensor from the mother tool and anchoring the first sensor at a first designated depth in the wellbore, and in a path of a first fluid flowing in the wellbore;
   moving the mother tool to a second designated depth in the wellbore and away from the first sensor;
   detaching the second sensor from the mother tool and anchoring the second sensor at the second designated depth in the wellbore, and in a path of a second fluid flowing in the wellbore;
   moving the mother tool away from the second sensor;
   sensing information about the first fluid with the first sensor;
   sensing information about the second fluid with the second sensor; and
   communicating the information about the first and second fluids from the first and second sensors to the mother tool and while the first and second sensors are anchored in the wellbore and detached from the mother tool.

2. The method of claim 1, further comprising moving the mother tool downhole unanchoring the first and second sensors from the wellbore, and reattaching the first and second sensors to the mother tool.

3. The method of claim 1, further comprising sensing a proximity between the mother tool and one of the first or second sensors when the one of the first or second sensors are decoupled from the mother tool, and using the sensed proximity to guide the mother tool to reattach with the one of the first or second sensors.

4. The method of claim 1, wherein the sensor comprises a plurality of sensors that are spaced apart from one another on the mother tool when the mother tool is deployed in the wellbore, and that are decoupled from the mother tool and anchored in the wellbore at different depths of the wellbore.

5. The method of claim 1, wherein the sensors communicate the information to the mother tool via wireless signals.

6. The method of claim 5, wherein the information comprises data selected from the group consisting of fluid type, fluid speed, fluid density, fluid viscosity, fluid pressure, fluid temperature, fluid acoustic properties, fluid electrical properties, fluid radioactive properties, fluid magnetic resonance properties, fluid optical properties, and an amount of fluid flow, and wherein the method further comprises sensing one or more of formation porosity and formation resistivity.

7. The method of claim 1, wherein the first sensor is disposed adjacent a first array of perforations, and wherein the second sensor is disposed adjacent a second array of perforations that is spaced a distance uphole from the first array of perforations.

* * * * *